United States Patent [19]

Jacobs et al.

[11] Patent Number: 4,756,882
[45] Date of Patent: * Jul. 12, 1988

[54] HYDROGEN PEROXIDE PLASMA STERILIZATION SYSTEM

[75] Inventors: Paul T. Jacobs; Szu-Min Lin, both of Arlington, Tex.

[73] Assignee: Surgikos Inc., Arlington, Tex.

[*] Notice: The portion of the term of this patent subsequent to Feb. 17, 2004 has been disclaimed.

[21] Appl. No.: 6,855

[22] Filed: Jan. 27, 1987

Related U.S. Application Data

[63] Continuation-in-part of Ser. No. 747,209, Jun. 21, 1985, Pat. No. 4,643,876.

[51] Int. Cl.⁴ ............................ A61L 2/14; A61L 2/18
[52] U.S. Cl. .......................................... 422/23; 422/28
[58] Field of Search ...................... 422/23, 28; 34/36

[56] References Cited

U.S. PATENT DOCUMENTS

| | | | |
|---|---|---|---|
| 3,383,163 | 5/1968 | Menashi | 422/23 |
| 3,701,628 | 10/1972 | Ashman | 422/23 |
| 3,851,436 | 12/1974 | Fraser et al. | 422/22 X |
| 3,948,601 | 4/1976 | Fraser et al. | 422/23 |
| 4,169,123 | 9/1979 | Moore et al. | 422/28 X |
| 4,169,124 | 9/1979 | Forstrom et al. | 422/28 X |
| 4,207,286 | 6/1980 | Gut Boucher | 422/28 X |
| 4,230,663 | 10/1980 | Forstrom et al. | 422/28 X |
| 4,289,728 | 9/1981 | Peel | 422/24 |
| 4,321,232 | 3/1982 | Bithell | 422/22 X |
| 4,348,357 | 9/1982 | Bithell | 422/22 |
| 4,366,125 | 12/1982 | Kodera et al. | 422/24 X |
| 4,368,081 | 1/1983 | Hata et al. | 422/30 X |
| 4,437,567 | 3/1984 | Jeng | 422/28 X |
| 4,643,876 | 2/1987 | Jacobs et al. | 422/28 X |

FOREIGN PATENT DOCUMENTS

| | | | |
|---|---|---|---|
| 19211 | 11/1980 | European Pat. Off. | 422/23 |
| 103460 | 6/1983 | Japan | 422/23 |
| 556813 | 6/1977 | U.S.S.R. | 422/23 |

OTHER PUBLICATIONS

Venugopalan, et al., Plasma Chemistry and Plasma Processing, 1(2), pp. 191-199 (1981).
Boucher, et al., "State of the Art in Gas Plasma Sterilization" MD & DI, Feb. (1985) pp. 51-56.

Primary Examiner—David L. Lacey
Assistant Examiner—Jill Johnston
Attorney, Agent, or Firm—Wayne R. Eberhardt

[57] ABSTRACT

A sterilization process wherein articles contacted with hydrogen peroxide and containing trace amounts of residual hydrogen peroxide are subjected to plasma treatment to generate an active species from the residual hydrogen peroxide which effects sterilization of the article and concurrently removes the residual hydrogen peroxide by converting it into non-toxic decomposition products.

16 Claims, 1 Drawing Sheet

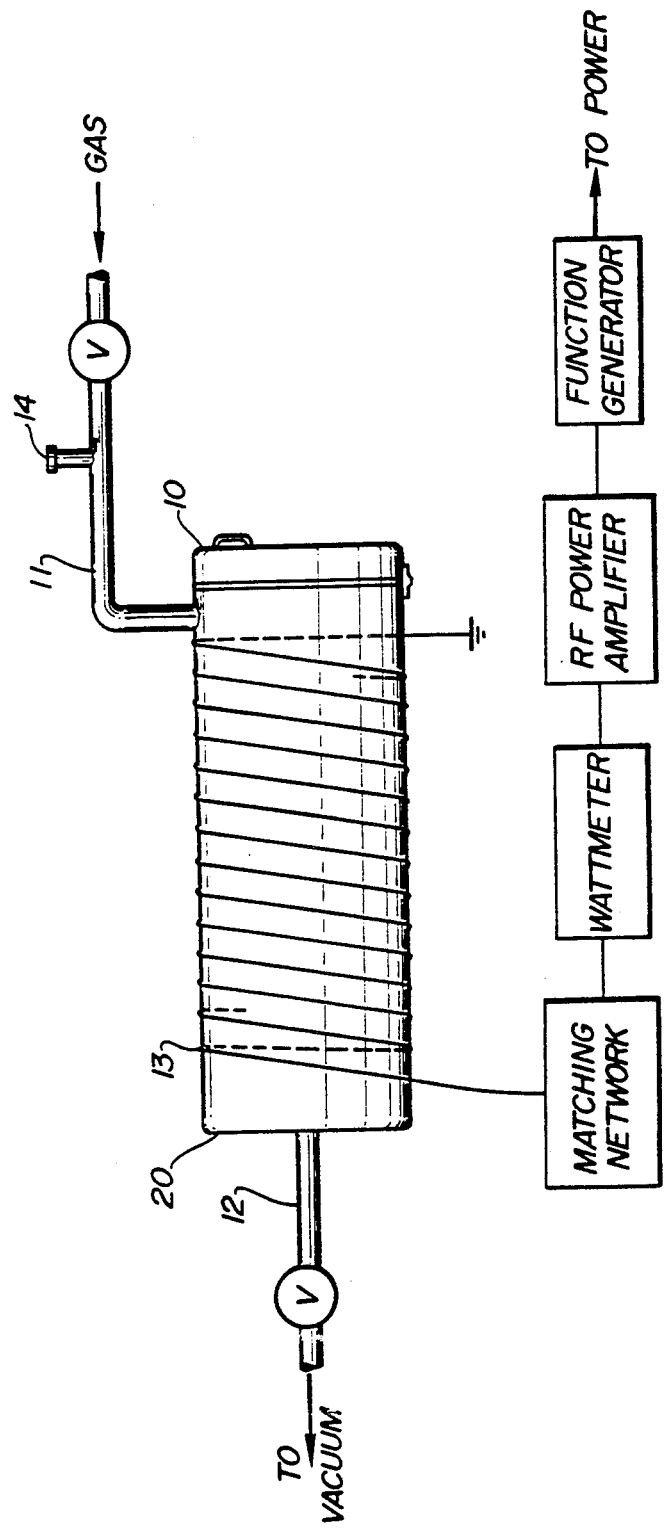

HYDROGEN PEROXIDE PLASMA STERILIZATION SYSTEM

CROSS-REFERENCE TO RELATED APPLICATIONS

This is a continuation-in-part of application Ser. No. 747,209, filed June 21, 1985, now U.S. Pat. No. 4,643,876.

FIELD OF THE INVENTION

The present invention relates to the sterilization of articles in gaseous plasmas and, more particularly, to the use of hydrogen peroxide in the plasma to kill microorganisms on surfaces ad objects such as medical instruments.

BACKGROUND OF THE INVENTION

Various methods of sterilization have been used in the past for the sterilization of different types of articles including disposable and reusable medical equipment, foods and food containers. Sterilization by steam or by dry heat has been extensively used in the past. Sterilization by heat, either wet or dry, is not useful to sterilize materials that are adversely effected by such heat or steam. Ethylene oxide gas has also been used but suffers from the drawback that it may leave toxic residues on the articles to be sterilized, which may have adverse effects, particularly on patients who come into contact with such articles. The extended aeration cycles required to remove residual ethylene oxide from some sterilized items also makes ethylene oxide sterilization excessively long.

The use of plasma to sterilize containers was suggested in U.S. Pat. No. 3,383,163. Plasma is an ionized body of gas which may be generated by the application of power from different sources. The ionized gas will contact microorganisms on the surface of the items to be sterilized and effectively destroy the microorganisms.

U.S. Pat. No. 3,851,436 discloses the use of radio frequency generators to produce such plasmas from inert gases such as argon, helium or xenon. U.S. Pat. No. 3,948,601 also discloses the use of a radio frequency generated plasma which ionizes argon, nitrogen, oxygen, helium or xenon. The processes set forth in the above-mentioned patent require the direct contact of the plasma on the surface of the product to be sterilized, which product is not packaged at the time of sterilization. The commercial sterilization procedures used to sterilize disposable medical goods generally require that the medical goods be packaged prior to sterilization because of the possibility of contamination by microorganisms if the products are packaged subsequent to sterilization.

U.S. Pat. No. 4,207,286 discloses a gas plasma sterilization system which uses glutaraldehyde as the gas which is used in a plasma sterilization system. The item to be sterilized is placed in an unsealed container or package and then subjected to the sterilization cycle. When the sterilization cycle is completed, the containers are sealed. The container must be opened during the sterilization cycle to allow the gas to flow into the interior of the package or container to allow contact of the gas with any microorganisms which may be on the surface of the item to be sterilized.

U.S. Pat. No. 4,321,232 discloses a plasma sterilization system in which the item to be sterilized is placed in a package made from a porous material. The gas used in the process is oxygen, and it is indicated that sterilization can be accomplished through the porous packaging within 60 minutes.

U.S. Pat. No. 4,348,357 discloses a plasma sterilization procedure using oxygen, nitrogen, helium, argon or freon as the gas. The pressure is pulsed, that is, the pressure within the container is alternately increased or decreased in a cyclic fashion. In addition, the plasma may be de-energized during the pressure fall portion of the pressure cycle to reduce the heating effect on the article to be sterilized.

Japanese Application Disclosure No. 103460-1983 discloses a plasma sterilization process in which the gas consists of nitrous oxide or a mixture of nitrous oxide with another gas such as oxygen, helium or argon. It is stated that the process can be used to sterilize through packaging and, particularly, packaging which is made from polyethylenetrifluoride or polyethylenetetrafluoride resins or paper coated with these materials.

Japanese Application Disclosure No. 162276-1983 discloses the sterilization of foods using nitrogen oxide gas or mixtures of nitrogen oxide gas and ozone in a plasma.

All of these prior plasma sterilization systems have not been put into wide commercial use because of the limitations on the time required to effect sterilization, the temperature obtained in the sterilization process or the particular requirements of some of the processes that would require post-sterilization packaging.

Hydrogen peroxide has been known to have bactericidal properties and has been used in solutions to kill bacteria on various surfaces. U.S. Pat. No. 4,437,567 discloses the use of aqueous hydrogen peroxide solutions at low concentrations, i.e., 0.01% to 0.10% by weight, to sterilize packaged products for medical or surgical use. At room temperature sterilization requires at least 15 days. At higher temperatures sterilization can be accomplished in approximately one day.

U.S. Pat. Nos. 4,169,123; 4,169,124 and 4,230,663 disclose the use of hydrogen peroxide in the gas phase at temperatures below 80° C. and concentrations of 0.10 to 75 mg $H_2O_2$ vapor/L for sterilization and disinfection. Depending upon concentration and temperature, sterilization times are reported to vary from 30 minutes to four hours.

The use of ultraviolet radiation with hydrogen peroxide for improved antimicrobial activity has been disclosed in U.S. Pat. Nos. 4,366,125 and 4,289,728. The lack of penetration by UV radiation below the surface of the object to be sterilized limits the application of this effect to clear solutions or surfaces that can be directly exposed to the radiation. Objects in an opaque package, or objects in a clear package that absorbs UV light could not be sterilized.

Food packaging materials sterilized with hydrogen peroxide contain hydrogen peroxide residuals that must be removed from the materials prior to use. U.S. Pat. No. 4,368,081 discloses the use of antioxidants or reducing agents such as L-ascorbic acid to remove residual hydrogen peroxide from a sterilized food package.

The combination of hydrogen peroxide and plasma has heretofore not been used for sterilization.

SUMMARY OF THE INVENTION

The present invention employs the use of hydrogen peroxide as a precursor of the active species in a low temperature plasma sterilization system. The sterilization process provides an initial contact of the material to be sterilized with the hydrogen peroxide before the generation of plasma at a power level sufficient to achieve sterilization. It has been found that the use of an initial contact period with hydrogen peroxide significantly decreases the total time and power required to accomplish sterilization with low temperature plasma. In addition, the use of the pre-treatment with hydrogen peroxide also allows sterilization to occur within many different types of packaging material.

Since the decomposition products of $H_2O_2$ in plasma include water, oxygen and hydrogen, no toxic residues remain on the sterilized items after plasma treatment.

BRIEF DESCRIPTION OF THE DRAWING

The FIGURE shows a schematic drawing of the plasma reactor used in the present invention.

DETAILED DESCRIPTION OF THE INVENTION

The process of the present invention differs from prior art gas plasma sterilization processes in two important aspects. The first is the use of hydrogen peroxide vapor as a precursor of the reactive species rather than an inert gas such as oxygen, nitrogen, etc. The second major difference is the use of a pre-treatment time where the hydrogen peroxide vapor is allowed to contact the article to be sterilized prior to the application of the power at levels required to effect sterilization. In the present process, the article to be sterilized is placed in the plasma chamber, the chamber is closed and vacuum is drawn on the chamber to remove the gas that is in the chamber. An aqueous solution of hydrogen peroxide is then injected into the chamber raising the pressure in the chamber to a level of approximately 0.1 to 10 Torr. The hydrogen peroxide remains in the chamber for a period of sufficient duration to allow the hydrogen peroxide to come in intimate contact with the item to be sterilized, normally five to 30 minutes, before the plasma is generated at a power level sufficient to achieve sterilization. The power then remains on for up to 50 minutes to allow complete sterilization, although sterilization can be effective in periods as short as 5 minutes from initial plasma generation, depending on the concentration of the hydrogen peroxide in the chamber and the power that is applied to the chamber. It is also possible to carry out the pre-treatment step outside of the plasma chamber. The object to be sterilized could be placed in a vacuum chamber in which plasma could not be generated. The chamber would be evacuated and the hydrogen peroxide injected into the vacuum chamber. The object to be sterilized would be kept in the vacuum chamber for the desired pre-treatment time and then placed in a plasma chamber and the plasma generated.

The materials or objects to be sterilized by the present process may be packaged in various commonly employed packaging materials used for sterilized products. The preferred materials are spunbonded polyethylene packaging material commonly available under the trademark "TYVEK" or composites of "TYVEK" with a polyethylene terephthalate packaging material commonly available under the trademark "MYLAR". Other similar packaging materials may also be employed. Paper packaging materials may also be used. With paper packaging, longer processing times may be required to achieve sterilization because of possible interactions of hydrogen peroxide and other reactive species with paper.

Plasmas are normally generated by electrical discharges in gases. Plasmas generated at atmospheric pressure or at higher pressures are called "arcs" or high temperature plasma and may involve temperatures in excess of 1000° C. Plasmas generated at reduced pressures, i.e., $10^{-3}$ to $10^2$ Torr, are called "glow discharge" or low temperature plasma and involve temperatures of a few tenths to a few hundred degrees Centigrade. The low temperature plasma of the present invention is preferably generated at pressures of less than 10 Torr and generally involves temperatures of less than 100° C.

When used in the present application, the term "plasma" is intended to include any portion of the gas or vapors which contains electrons, ions, free radicals, dissociated and/or excited atoms or molecules produced as a result of the applied electrical field including any accompanying radiation which might be produced. The applied field may cover a broad frequency range, however, a radio frequency is commonly used.

Plasma sterilization is usually carried out in a chamber 20 as illustrated in FIG. 1. The chamber includes a door or opening 10 through which articles to be sterilized can be introduced. The chamber also includes an inlet 11 to inject gas into the chamber and a line 12 connected to a vacuum pump to enable the chamber to be evacuated. There is a port 14 in the gas inlet line 11 to introduce the aqueous solution of hydrogen peroxide into the chamber 20. The chamber includes radio frequency electrodes 13 which can be wound around the entire chamber or placed on the sides of the chamber and a radio frequency generator to generate the requisite radio frequency signal. Coupling of RF power from the output of the matching network to the discharge is accomplished by means of either a coil or a set of capacitor plates. These two forms of coupling are referred to as inductive and capacitive coupling, respectively. Various control devices which control the generation of the radio frequency signal including function generators, RF power amplifiers, wattmeter and matching network are also employed and are illustrated in FIG. 1. The matching network matches the input of the amplified RF signal into the coil. The plasma is generated by evacuating the chamber, introducing a gas or vaporized liquid and turning on the power to the electrodes. The plasma is generated in the present process in the same manner as in the previously-mentioned prior art plasma sterilization system.

The plasma used in the present process may be continuous or pulsed, that is, the power may be applied continuously to the plasma or the plasma may be pulsed by activating the power in a cyclic manner while maintaining the pressure of the plasma constant. The use of a pulsed plasma prevents the overheating of the gas within the chamber as well as preventing the overheating of objects that may be desired to be sterilized. The pulsed sequence may vary over a fairly wide range without the danger of overheating any object. Generally, the pulsing sequence is the ratio of power on to power off. For example with a 1:2 pulsed plasma, power would be applied for 0.5 milliseconds and then turned off and applied again 1.0 milliseconds later. The particular pulsing sequence is not critical. The power may be applied for periods measured in minutes rather than seconds. The purpose of pulsing is to avoid overheating of the objects to be sterilized, and any pulsing sequence that avoids overheating and sterilizes in a reasonable time period may be employed. Continous plasma may be employed if there is little danger of overheating the item to be sterilized.

As previously indicated, in the present process the hydrogen peroxide is injected into the plasma chamber prior to the application of the power necessary to sterilize. The hydrogen peroxide is injected in the form of an aqueous solution of hydrogen peroxide containing from about 3% to 20% by weight of hydrogen peroxide. The concentration of hydrogen peroxide vapor in the chamber may range from 0.05 to 10 mg of hydrogen peroxide per liter of chamber volume. The higher concentrations of hydrogen peroxide will result in shorter sterilization times. A concentration of 0.125 mg per liter is the minimum preferred concentration of hydrogen peroxide. Air or an inert gas such as argon, helium, nitrogen, neon or xenon may be added to the chamber with the hydrogen peroxide to maintain the pressure in the chamber at the desired level. The hydrogen peroxide solution may be injected in one or more separate injections. For example, at time "zero" one-half of the total amount of hydrogen peroxide solution to be used could be injected into the chamber, and five minutes later the remainder of the hydrogen peroxide solution can be injected. The hydrogen peroxide would then remain in the chamber before power was applied for an additional five to ten minutes. Apparently, the pre-treatment time allows the hydrogen peroxide to diffuse through the packaging material and come into close proximity, if not contact, with the surface of the item to be sterilized. Upon the application of power to the radio frequency generator, sporicidally active species are generated by the combination of hydrogen peroxide and plasma, and, therefore, the time required to effect sterilization is shorter than in prior art processes. It is possible to generate plasma at low power levels during the pre-treatment cycle, but there is no particular advantage in applying power during the pre-treatment cycle.

Although the exact mechanism of the sporicidal activity is not known with certainty, in an electrical discharge hydrogen peroxide can be dissociated into free radicals, i.e., OH, $O_2H$, H (M. Venugopalan and A. Shih, *Plasma Chemistry and Plasma Processing*, Vol 1, No. 2, pages 191-199, 1981). These free radicals, either alone or in combination with hydrogen peroxide, are probably the primary source of sporicidal activity. Ultraviolet radiation is also produced in a low temperature plasma and may play a role in sporicidal activity, especially in the presence of hydrogen peroxide.

The general operation of the present process is as follows:

(1) The object or article to be sterilized is placed in a vacuum chamber or into the plasma chamber.

(2) The chamber is evacuated to a pressure of approximately 0.05 Torr.

(3) An aqueous solution of hydrogen peroxide is injected into the chamber to a pressure of vaporized water and hydrogen peroxide of from 0.5 to 10 Torr. The preferred pressure is from 1 to 2 Torr. The concentration of the hydrogen peroxide injected into the chamber may be from about 0.05 to 10 mg/liter of chamber volume. The preferred concentration is 0.208 mg/liter.

(4) The object to be sterilized is held in the chamber before plasma with sufficient power to sterilize is generated for a period of from about 5 to 30 minutes. This period is referred to herein as the pre-treatment time. Pre-treatment times longer than 30 minutes may be employed. The duration of the pre-treatment time may depend on the type of package used, the number of items to be sterilized, and the placement of the items in the chamber.

(5) The object to be sterilized is subjected to a plasma either in the pre-treatment chamber or in a separate plasma chamber.

(6) The RF energy used to generate the plasma may be continuous or it may be pulsed. The object remains in the plasma for a period of from 5 to 60 minutes to effect complete sterilization.

Since the hydrogen peroxide is decomposed into non-toxic products during the plasma treatment, no additional steps are required to remove residual hydrogen peroxide from the sterilized object or its packaging prior to use of the object.

In the following examples, the effectiveness of the sterilization cycle is expressed as the ratio of the number of organisms surviving the test (S) to the initial number of organisms which were placed on the specimen prior to the test (SO). In all of these examples, the organisms tested was *Bacillus subtilis* (var. Globigii) spores which were placed on paper discs and packaged in a spun-bonded polyethylene package. All examples were conducted in a 5.5 liter plasma chamber operating at a frequency of 2.49 MHz, except for Example V which was conducted at a frequency of 3.89 MHz

EXAMPLE 1

Table I contains a comparison of the sporicidal activity of the present hydrogen peroxide/plasma system to other prior art gases in the present plasma cycle. All tests were run under the same reaction conditions, i.e., 150 watts of pulsed plasma in a cycle of 0.5 milliseconds plasma on, 1.0 milliseconds plasma off for 15 minutes. All tests employed in a 10 minute pre-treatment cycle with the gas listed in the Table. All pre-treatments and plasma treatments occurred at 1.5 Torr pressure. The glutaraldehyde and hydrogen peroxide pre-treatment cycle contained 0.208 mg/liter of glutaraldehyde and hydrogen peroxide, respectively. The results are expressed as S/SO in which S is the number of surviving organisms and SO is the initial number of organisms.

TABLE I

SPORICIDAL ACTIVITY OF $H_2O_2$/PLASMA SYSTEM COMPARED TO OTHER GAS/PLASMA SYSTEMS

| Gas | Sporicidal Activity S/SO |
|---|---|
| $O_2$ | $9.1 \times 10^5 / 1.3 \times 10^6 = 0.72$ |
| $N_2O$ | $4.9 \times 10^4 / 1.6 \times 10^5 = 0.31$ |
| Glutaraldehyde | $5.7 \times 10^4 / 1.1 \times 10^5 = 0.52$ |
| $H_2O_2$ | $0 / 3.4 \times 10^5 = 0$ |

Only the hydrogen peroxide/plasma system exhibited good sporicidal activity and sterilized the treated item.

EXAMPLE II

The effect of hydrogen peroxide concentration in the plasma chamber on sporocidal activity was determined by pre-treating test samples with hydrogen peroxide vapor of different concentrations at 1.0 Torr pressure for ten minutes. The treated samples were then exposed to 200 watts of pulsed plasma in a cycle of 0.5 milliseconds plasma on and 1.0 milliseconds plasma off for 15 minutes. Two controls, one using only hydrogen peroxide and one using only water plasma, were also run. The results are shown in Table II.

TABLE II
EFFECT OF H$_2$O$_2$ CONCENTRATION ON SPORICIDAL ACTIVITY

| Conc. H$_2$O$_2$ (mg H$_2$O$_2$/liter) | SPORICIDAL ACTIVITY H$_2$O$_2$ Alone (S/SO) | H$_2$O$_2$ + Plasma (S/SO) |
|---|---|---|
| 0* | 1.0 | 1.0 |
| .125 | 1.0 | 7.3 × 10$^{-2}$ |
| .208 | 1.0 | 1.4 × 10$^{-2}$ |
| .416 | 1.0 | 0** |
| .625 | 9.1 × 10$^{-2}$ | 0** |

*A plasma containing 4.16 mg H$_2$O/liter was used in this test.
**Total kill of 2.4 × 10$^5$ organisms.

No significant sporicidal activity was obtained with the water plasma treatment alone, or with H$_2$O$_2$ alone at concentrations below 0.625 mg/liter. However, a significant enhancement in sporicidal activity was obtained with the H$_2$O$_2$/plasma combination at all H$_2$O$_2$ concentration evaluated.

EXAMPLE III

The effect of pressure on sporicidal activity was determined using a hydrogen peroxide concentration of 0.208 mg/liter and the same pre-treatment and plasma cycle as in Example II. The activity was determined at pressures of 0.5, 1.0, 1.5 and 2.0 torr. The activity of air plasma only and hydrogen peroxide only were also determined. The results of these experiments are reported in Table III.

TABLE III
EFFECT OF PRESSURE ON SPORICIDAL ACTIVITY OF H$_2$O$_2$ PLASMA

| Pressure (Torr) | Plasma Only (S/SO) | H$_2$O$_2$ Only (S/SO) | SPORICIDAL ACTIVITY H$_2$O$_2$ + Plasma (S/SO) |
|---|---|---|---|
| 0.5 | 6.0 × 10$^{-1}$ | 9.6 × 10$^{-1}$ | 4.1 × 10$^{-1}$ |
| 1.0 | 6.7 × 10$^{-1}$ | 1.0 | 1.4 × 10$^{-2}$ |
| 1.5 | 2.8 × 10$^{-1}$ | 3.9 × 10$^{-1}$ | 0* |
| 2.0 | 2.4 × 10$^{-1}$ | 6.6 × 10$^{-1}$ | 1.9 × 10$^{-4}$ |

*Total kill of 3.4 × 10$^5$ organisms.

A low level of activity was obtained with either plasma only or H$_2$O$_2$ only at all pressures. The optimum activity with the H$_2$O$_2$ plus plasma system was obtained at 1.5 Torr pressure.

EXAMPLE IV

The effect of plasma power on sporicidal activity was determined using a hydrogen peroxide concentration of 0.208 mg H$_2$O$_2$/liter at a pressure of 1.5 Torr. The power levels were 50, 100, 150 and 200 watts. The plasma was pulsed as in Example II, and the samples were pre-treated for 10 minutes with the procedure used in Example II. Air plasma only and hydrogen peroxide only test were also run. The results are shown in Table IV.

TABLE IV
EFFECT OF RF POWER LEVEL ON SPORICIDAL ACTIVITY OF AIR PLASMA AND H$_2$O$_2$ PLUS PLASMA

| Power (Watts) | SPORICIDAL ACTIVITY Plasma Only (S/SO) | H$_2$O$_2$ + Plasma (S/SO) |
|---|---|---|
| 0 | 1.0 | 4.0 × 10$^{-1}$ |
| 50 | 4.0 × 10$^{-1}$ | 8.1 × 10$^{-1}$ |
| 100 | 6.7 × 10$^{-1}$ | 2.5 × 10$^{-3}$ |
| 150 | 2.4 × 10$^{-1}$ | 0* |
| 200 | 3.9 × 10$^{-1}$ | 0* |

*Total kill of 1.8 × 10$^5$ organisms.

A low level of sporicidal activity was obtained with air plasma alone at all power loads evaluated. Significant sporicidal activity was obtained with the H$_2$O$_2$ plus plasma system at 100 watts power, and sterilization was achieved at 150 and 200 watts power.

EXAMPLE V

The effect of plasma generation during the hydrogen peroxide pre-treatment time on sporicidal activity was determined using a hydrogen peroxide concentration of 0.208 mg H$_2$O$_2$/liter at a pressure of 1.5 Torr. During the 10 minute hydrogen peroxide pre-treatment time 50, 75, 100, 125 and 150 watts of power were applied at 3.89 MHz. The plasma was pulsed in a cycle of 0.5 milliseconds power on to 1.0 milliseconds power off. After the 10 minute pre-treatment time, all samples were exposed to 150 watts of power pulsed 0.5 milliseconds on to 1.0 milliseconds off for 15 minutes. The results of this test are shown in Table V.

TABLE V
EFFECT OF RF POWER LEVEL DURING PRE-TREATMENT ON SPORICIDAL ACTIVITY OF H$_2$O$_2$ PLUS PLASMA

| Power Level During Pretreatment (Watts) | Sporicidal Activity (S/SO) |
|---|---|
| 50 | 9.4 × 10$^{-5}$ |
| 75 | 1.2 × 10$^{-4}$ |
| 100 | 1.0 |
| 125 | 0.83 |
| 150 | 0.94 |

Significant sporicidal activity was obtained when low power levels, i.e., 50 and 75 watts, were applied during the hydrogen peroxide pre-treatment time. At higher power levels, which would dissociate more of the hydrogen peroxide before it could diffuse to the sample, very limited sporicidal activity was observed.

EXAMPLE VI

The effect of pulsing the plasma power on the sporicidal activity was determined using a hydrogen peroxide concentration of 0.208 mg H$_2$O$_2$/liter and a pressure of 1.5 Torr. Samples were pre-treated with hydrogen peroxide for 10 minutes as in Example II. Air plasma only and hydrogen peroxide only tests were also run. As in previous tests, the hydrogen peroxide only test gave an S/SO value of approximately 4.0x10$^{-1}$. The results of the testes with 100 watts of continuous plasma for 5 minutes, and 150 watts of plasma pulsed in a cycle of 0.5 milliseconds plasma on, and 1.0 milliseconds plasma off for 15 minutes are presented in Table VI.

TABLE VI

EFFECT OF PLASMA PULSING ON SPORICIDAL ACTIVITY

| Plasma Condition | Plasma Only (S/SO) | $H_2O_2$ + Plasma (S/SO) |
|---|---|---|
| 5 minute 100 watts Continuous Plasma | $3.4 \times 10^{-1}$ | 0* |
| 15 minute 150 watts 1:2 pulsed plasma | $2.4 \times 10^{-1}$ | 0* |

*Total kill of $2.2 \times 10^5$ organisms

The results of these tests illustrate that sterilization can be achieved within five minutes with a continuous plasma treatment.

EXAMPLE VII

The effect of repeat $H_2O_2$/plasma treatments on the sporicidal activity was determined using a hydrogen peroxide concentration of 0.125 mg/liter and a pressure of 1.5 Torr. Each treatment cycle consisted of a 10 minute pre-treatment time with $H_2O_2$ and a 15 minutes exposure to 200 watts of pulsed plasma (0.5 milliseconds plasma on and 1.0 milliseconds plasma off). The effect of one and two treatement cycles are presented in Table VII.

TABLE VII

EFFECT OF NUMBER OF $H_2O_2$/PLASMA CYCLES ON SPORICIDAL ACTIVITY

| | Sporicidal Activity | | |
|---|---|---|---|
| No. Cycles | $H_2O_2$ Alone (S/SO) | Plasma Alone (S/SO) | $H_2O_2$ + Plasma (S/SO) |
| 1 | $5.9 \times 10^{-1}$ | $6.6 \times 10^{-1}$ | $8.8 \times 10^{-3}$ |
| 2 | $8.2 \times 10^{-1}$ | $1.8 \times 10^{-1}$ | 0* |

*Total kill of $2.5 \times 10^5$ organisms.

These results illustrate that sterilization can be achieved at low $H_2O_2$ concentrations by exposing the sample to two $H_2O_2$/plasma treatment cycles.

The above examples demonstrate the effectiveness of the use of hydrogen peroxide as the precursor of the reactive species in a plasma sterilization process. The operating parameters of the process, i.e., hydrogen peroxide concentration, pre-treatment cycle, power applied and time duration of plasma generation can be varied within farily wide limits to produce an adequate sterilization cycle. The power applied or the hydrogen peroxide concentration may be reduced if the duration of plasma generation is increased, and, similarly, the duration of the plasma generation can be decreased if the concentration of hydrogen peroxide or the power applied is increased.

EXAMPLE VIII

Because items exposed to plasma increase in temperature, an experiment was conducted to compare the sporicidal activity obtained with hydrogen peroxide and heat to that obtained with hydrogen peroxide and plasma. This test was conducted by placing samples inside and outside a wire cage in the plasma chamber. Since metals effectively shield RF radiation, the sample inside the wire cage was shielded from RF radiation and plasma formation but not from exposure to hydrogen peroxide vapor or the heat generated by the plasma. The samples were treated with 0.208 mg hydrogen peroxide/liter at 1.5 Torr pressure for 10 minutes. The treated samples were then exposed to 150 watts of pulsed plasma in a cycle of 0.5 milliseconds plasma on and 1.0 milliseconds plasma off for 15 minutes. The temperature of nylon blocks located inside and outside the wire cage was monitored with a Luxtron Model 1000A, FLUOROPTIC TM Thermometer. At the end of the plasma treatment the temperature recorded inside and outside the wire cage was 52.1° C. and 56.9° C. respectively. The sporicidal test results are presented in Table VIII. A control experiment with hydrogen peroxide vapor only was also run.

TABLE VIII

A COMPARISON OF SPORICIDAL ACTIVITY WITH HYDROGEN PEROXIDE AND HEAT AND HYDROGEN PEROXIDE AND PLASMA

| | Sporicidal Activity | |
|---|---|---|
| Conditions | Inside cage (S/SO) | Outside cage (S/SO) |
| $H_2O_2$ Vapor | $4.2 \times 10^{-1}$ | $3.3 \times 10^{-1}$ |
| $H_2O_2$ + Plasma | $2.4 \times 10^{-1}$ | 0** |

**Total kill of $3.0 \times 10^5$ spores.

These results illustrate that significantly better sporicidal activity was obtained outside than inside the wire cage with the combination of hydrogen peroxide and and plasma. The reduced sproricidal activity inside the wire cage should largely be due to the absence of plasma formation since similar sporicidal activity was obtained with hydrogen peroxide alone inside and outside the cate, and after plasma treatment the temperatures inside and outside the wire cage were similar.

EXAMPLE IX

In an alternative embodiment of the present invention, the item to be sterilized may be pretreated with a solution of hydrogen peroxide, and then exposed to plasma to achieve sterilization. The pretreatment can be achieved by dipping or spraying the item to be sterilized with the hydrogen peroxide solution while maintaining the hydrogen peroxide solution in contact with the item for a time sufficient to assure direct contact of the spores with the $H_2O_2$. After removing the treated items from the hydrogen peroxide solution, the items, which retain traces of residual hydrogen peroxide, are subjected to plasma treatment as hereinbefore described except that no hydrogen peroxide solution is required to be injected into the plasma chamber.

The effect of pretreating an item with hydrogen peroxide solution was demonstrated by placing stainless steel surgical blades contaminated with *Bacillus subtilis* (var. Globigii) in aqueous 3% $H_2O_2$ solution for times varying from 5 to 60 minutes. After the treatment, the blades were removed from the solution, blotted with aborbent paper to remove excess solution, and exposed to 150 watts of pulsed plasma in a cycle of 0.5 milliseconds on, 1.0 milliseconds off for a period of 15 minutes. A portion of the hydrogen peroxide treated blades were sealed in Tyvek packaging prior to the plasma treatment. The residual sporicidal activity of the packaged and unpackaged blades was compared to that of blades which had been contacted with the hydrogen peroxide solution but not subjected to the plasma treatment. The results are shown in Table IX.

TABLE IX
EFFECT OF $H_2O_2$ CONCENTRATION ON SPORICIDAL ACTIVITY

| $H_2O_2$ Conc. % | Pretreat. Time Min. | $H_2O_2$ Alone | Sporicidal Activity $H_2O_2$ + Plasma Unpackaged | Sporicidal Activity $H_2O_2$ + Plasma Packaged |
|---|---|---|---|---|
| 0 | 5 | $9.6 \times 10^{-1}$ | $1.7 \times 10^{-3}$ | $2.4 \times 10^{-1}$ |
|   | 30 | $9.3 \times 10^{-1}$ | $1.8 \times 10^{-3}$ | $3.8 \times 10^{-1}$ |
|   | 60 | $9.5 \times 10^{-1}$ | $8.9 \times 10^{-4}$ | $1.1 \times 10^{-1}$ |
| 3 | 5 | $9.3 \times 10^{-1}$ | $1.4 \times 10^{-6}$ | $6.2 \times 10^{-2}$ |
|   | 30 | $7.2 \times 10^{-1}$ | $2.2 \times 10^{-6}$ | $3.4 \times 10^{-3}$ |
|   | 60 | $7.4 \times 10^{-1}$ | 0* | 0* |
| 6 | 5 | $5.5 \times 10^{-1}$ | $3.2 \times 10^{-7}$ | $3.2 \times 10^{-7}$ |
|   | 30 | $4.1 \times 10^{-1}$ | 0* | $3.1 \times 10^{-7}$ |
|   | 60 | $2.4 \times 10^{-1}$ | 0* | 0* |
| Air Plasma Control | | | $5.7 \times 10^{-4}$ | $3.7 \times 10^{-1}$ |

*Total kill of $1.9 \times 10^6$ organisms.

The above results indicate that the plasma treatment of items which have been pretreated with $H_2O_2$ solution is more effective in reducing sporicidal activity than treatment with $H_2O_2$ solution alone, and that sporocidal effectiveness of the treatment method generally increases as the concentration of hydrogen peroxide and soaking time are increased. The data further illustrate that plasma treatment alone in the absence of $H_2O_2$ pretreatment is also less effective in sporicidal activity.

As previously described, hydrogen peroxide in the liquid or vapor phase may be used as an effective sterilant in the absence of plasma treatment. Such sterilization may require higher concentrations of $H_2O_2$, higher temperatures, or longer exposure times than are employed with process of the present invention. When utilizing hydrogen peroxide sterilization, care must be taken to remove all traces of $H_2O_2$ from the sterilized items. In this regard, plasma treatment in accordance with the present invention is useful as an aftertreatment to remove $H_2O_2$ residuals as illustrated by the following example.

EXAMPLE X

Paper disks in a Tyvek package were vapor sterilized by exposure to 0.42 mg $H_2O_2$/liter for 15 minutes, after which the average concentration of hydrogen peroxide that remained on the disk was determined to be 381 micrograms. The samples were then treated for up to 60 minutes with either a vacuum at 0.03 Torr or 150 watt 1:2 pulsed plasma at 0.5 Torr, and the residual $H_2O_2$ remaining on the paper disks again determined with the results as shown in Table X.

TABLE X
REMOVAL OF RESIDUAL $H_2O_2$

| Treatment Time (Min) | Residual $H_2O_2$ (micrograms) Vacuum only at 0.03 Torr | Residual $H_2O_2$ (micrograms) Plasma at 0.5 Torr |
|---|---|---|
| 0 | 381 | 381 |
| 5 | N/D | 157 |
| 10 | N/D | 71 |
| 15 | 368 | 20 |
| 60 | 365 | N/D |

N/D = not determined

The above data demonstrates that the plasma treatment was more effective in removing residual hydrogen peroxide than vacuum alone.

As noted previously, the decomposition products of $H_2O_2$ in plasma include water, oxygen and hydrogen, and no toxic residues remain on the sterilized items after plasma treatment. The present invention accordingly includes the process of sterilization wherein actual sterilization is achieved by treatment with $H_2O_2$ in the absence of plasma, followed by treatment with plasma to remove residual traces of hydrogen peroxide.

We claim:

1. A process of plasma sterilization using hydrogen peroxide as a precursor of the active species in the plasma comprising the steps of
   contacting the item to be sterilized with a liquid hydrogen peroxide solution,
   placing the item into a sterilization chamber, said item retaining residual hydrogen peroxide.
   generating a plasma around the item within the sterilization chamber to generate an active species from said residual hydrogen peroxide,
   maintaining the item in said plasma for a time period sufficient to effect sterilization by said active species of said residual hydrogen peroxide.
2. The process of claim 1 wherein said item is maintained in said plasma until the residual hydrogen peroxide is decomposed into nontoxic products.
3. The process of claim 1 wherein the plasma is generated around the item for a period of time about 5 to 60 minutes.
4. The process of claim 1 wherein said plasma is pulsed at a power-on-power-off ratio of 1:2.
5. The process of claim 1 wherein said plasma is generated at a pressure of from about 0.1 to 10 Torr.
6. The process of claim 1 wherein said plasma is generated at a power of from about 50 to 200 watts.
7. The process of claim 1, including the further step of packaging said item containing residual hydrogen peroxide before said item is placed in said sterilization chamber.
8. The process of claim 1 wherein said item is contacted with an aqueous solution of said hydrogen peroxide.
9. The process of claim 8 wherein said aqueous solution contains from about 1 to 10 percent hydrogen peroxide, by weight.
10. The process of claim 8 wherein said item is contacted for a time of from about 1 minute to 1 hour.
11. A process of removing residual hydogen peroxide from items which have been sterilized by exposure to hydrogen peroxide which comprises placing said sterile item containing residual hydrogen peroxide into a plasma chamber and generating a plasma around said item for a period of time sufficient to decompose said residual hydrogen peroxide into nontoxic decomposition products.
12. The process of claim 11 wherein said plasma is generated for a period of from about 5 to 60 minutes.
13. The process of claim 11 wherein said plasma is pulsed at a power-on-power-off ratio of 1:2.
14. The process of claim 11 wherein said plasma is generated at a pressure of from about 0.1 to 10 Torr.
15. The process of claim 11 wherein said plasma is generated at a power of from about 50 to 200 watts.
16. The process of claim 11 wherein said sterile item is contained in a package.